United States Patent
Bohl et al.

(10) Patent No.: US 10,772,616 B2
(45) Date of Patent: Sep. 15, 2020

(54) NON-METALLIC RETRACTOR DEVICE WITH SWIVEL RETRACTOR ARMS

(71) Applicant: Dignity Health, San Francisco, CA (US)

(72) Inventors: Michael Bohl, San Francisco, CA (US); Zachary Hanze, San Francisco, CA (US); Kevin Baumann, San Francisco, CA (US); Megan Pottinger, San Francisco, CA (US); David Xu, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 16/463,650

(22) PCT Filed: Nov. 22, 2017

(86) PCT No.: PCT/US2017/063088
§ 371 (c)(1),
(2) Date: May 23, 2019

(87) PCT Pub. No.: WO2018/098337
PCT Pub. Date: May 31, 2018

(65) Prior Publication Data
US 2019/0374214 A1 Dec. 12, 2019

Related U.S. Application Data

(60) Provisional application No. 62/425,712, filed on Nov. 23, 2016, provisional application No. 62/514,074, filed on Jun. 2, 2017.

(51) Int. Cl.
*A61B 17/02* (2006.01)
*A61B 17/00* (2006.01)
*A61M 27/00* (2006.01)

(52) U.S. Cl.
CPC ...... *A61B 17/0218* (2013.01); *A61B 17/0206* (2013.01); *A61B 2017/00407* (2013.01); *A61B 2017/00526* (2013.01); *A61M 27/002* (2013.01)

(58) Field of Classification Search
CPC ...................... A61B 17/0218; A61B 17/0206
See application file for complete search history.

(56) References Cited

U.S. PATENT DOCUMENTS 4,421,107 A 12/1983 Estes
4,702,230 A * 10/1987 Pelta .................. A61B 17/0206
 403/362
5,976,171 A * 11/1999 Taylor ................ A61B 17/0206
 600/201

(Continued)

FOREIGN PATENT DOCUMENTS

DE 29806973 U1 8/1998
GB 674272 A 6/1952

OTHER PUBLICATIONS

International Search Report and Written Opinion from corresponding Application No. PCT/US2017/063088, dated Jan. 30, 2018, 9 pages.

*Primary Examiner* — Christian A Sevilla
(74) *Attorney, Agent, or Firm* — Polsinelli PC

(57) ABSTRACT

Various embodiments of a non-metal retractor device for retracting an incision and retaining a shunt are described herein.

20 Claims, 9 Drawing Sheets

(56) References Cited

U.S. PATENT DOCUMENTS

| | | | |
|---|---|---|---|
| 6,290,644 B1* | 9/2001 | Green, II | A61B 17/00234 600/209 |
| 6,309,349 B1* | 10/2001 | Bertolero | A61B 1/313 600/210 |
| 2002/0016527 A1* | 2/2002 | Hancock | A61B 17/0206 600/213 |
| 2003/0069479 A1* | 4/2003 | Phillips | A61B 17/02 600/228 |
| 2005/0096646 A1 | 5/2005 | Wellman | |
| 2008/0073922 A1 | 3/2008 | Holtz | |
| 2008/0077171 A1* | 3/2008 | Blain | A61B 17/0206 606/190 |
| 2014/0316209 A1 | 10/2014 | Overes et al. | |

* cited by examiner

NON-METALLIC RETRACTOR DEVICE WITH SWIVEL RETRACTOR ARMS

FIELD

The present disclosure generally relates to a surgical instrument, and in particular to an improved retractor device configured to retract incisions on a subject's body and retain catheters or shunt tubing in place during surgical procedures.

BACKGROUND

Certain surgical procedures require retraction of soft tissue and a shunt to remove bodily fluids. Hydrocephalus, for example, is a condition caused by buildup of excess cerebrospinal fluid (CSF) in the ventricles of the brain. The increased size of the ventricles causes excess pressure on brain tissue. Symptoms may vary with age, disease progression, and individual differences, but in some cases may be fairly severe and lead to seizures, mental impairment, or death.

A common procedure to address this condition involves the formation of a surgical incision to access the excess fluid. The incision may be held open by a locking retractor tool such as a retractor device; however, conventional retractor devices have various drawbacks. Retractor devices are generally reusable and costs for each device may range anywhere from $100 to $500; with significant further costs being incurred during sterilization and maintenance. Surgical retractors are commonly made from metals such as stainless steel or anodized aluminum.

To remove the excess CSF, the procedure may further include the placement of a ventriculoperitoneal (VP) shunt to drain the excess fluid from the brain into the abdomen, blood vessels, pleura, or a number of other potential spaces in the human body. The shunt may include a ventricular catheter that is inserted into one of the brain's ventricles with a portion of the catheter remaining extracranial. This catheter is typically referred to as the proximal catheter. The extracranial end of the proximal catheter is typically attached to an adjustable valve that regulates the flow of fluid out of the ventricles. The shunt also includes a distal catheter that most often drains into the peritoneal space. This catheter is connected to the distal end of the valve, is tunneled underneath the skin, and drains into the abdomen where the fluid is then reabsorbed. During surgical placement of the proximal catheter, the intracranial pressure and/or gravity can cause this catheter to move into or out of the brain. There is also a risk of overdraining the ventricles once the proximal catheter is placed, requiring occlusion of the extracranial end of the catheter until it is connected to the inlet port of the valve.

Electromagnetic navigation guidance systems (EM systems) are often used throughout the same procedure to ensure correct placement of the proximal catheter into one of the brain's ventricles. EM systems rely upon magnetic fields to relay information to the surgeon about where in space certain surgical instruments, such as stylets inserted through the proximal catheter, are positioned in relation to the patient. Yet, EM systems often malfunction when metallic materials are used in close proximity. Thus, conventional metal retractor devices can cause a loss of catheter visualization during the most crucial parts of the procedure. Further, as described herein, the proximal catheter may migrate in or out of the brain during the procedure, or overdrain the brain's CSF if not properly secured after intracranial placement.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
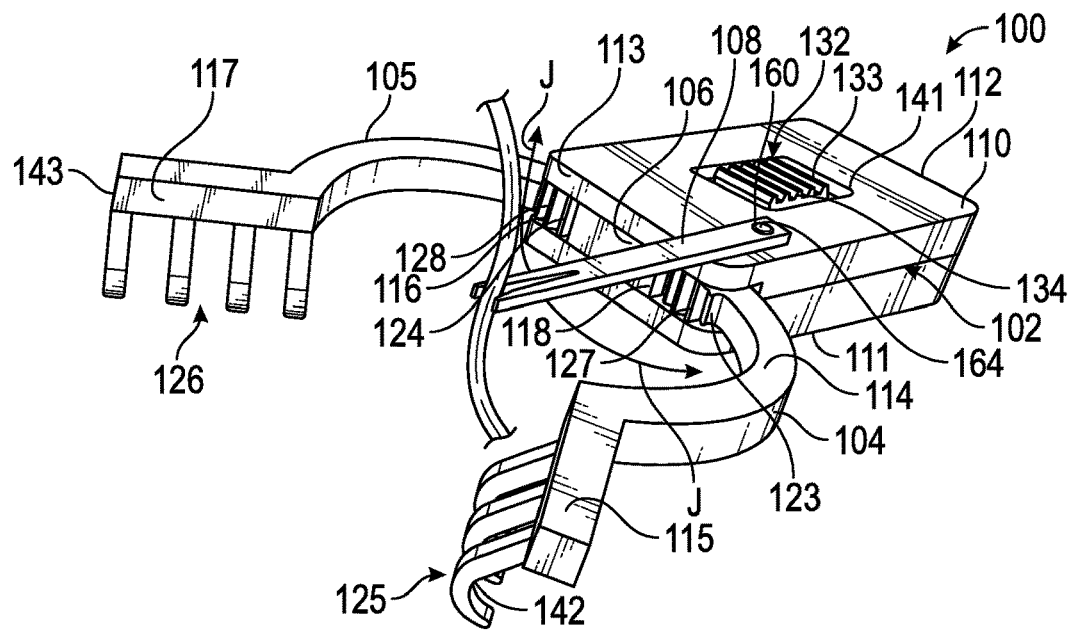
FIG. 1 is a perspective view of an embodiment for a retractor device, according to aspects of the present disclosure.

Various embodiments of a retracting device for retracting an incision and retaining a shunt catheter or other tubing, or other medical equipment, are described herein. In some embodiments, the retractor device defines a retractor body operatively coupled to a first retractor arm and an opposing second retractor arm which are movable relative to the retractor body to retract an incision. In some embodiments, the first and second retractor arms are in operative engagement with a sliding rail that is disposed within the retractor body and is operable to swivel the first and second retractor arms between closed and open positions during movement (e.g., linear sliding movement) of the sliding rail along a plurality of predetermined positions formed along the retractor body. In some embodiments, the retractor device is manufactured entirely from a non-metallic material such as a glass fiber composite. In some embodiments, a shunt retainer may be coupled to the retractor device along the retractor body for controlling movement of a catheter or shunt tubing during surgery. Referring to the drawings, embodiments of a retractor device are illustrated and generally indicated as 100 and 200 in FIGS. 1-22.

Referring to FIGS. 1-8, an embodiment of the retractor device 100 is configured to engage and retract an incision along the skin, muscle or other bodily tissues or combinations thereof, as described herein. The retractor device 100 may include a retractor body 102 having a top portion 110 attached to a bottom portion 111 that collectively define a proximal end 112 (not visible in FIG. 5) and a distal end 113 of the retractor body 102. In addition, the retractor body 102 is operatively connected to a first retractor arm 104 and an opposing second retractor arm 105 that are operable to swivel between a closed position (FIG. 10) and an open position (FIG. 12) including any positions (FIG. 11) there between when engaging and retracting bodily tissue. As shown, the retractor body 102 is operatively connected to a sliding rail 106 that is operable to swivel the first and second retractor arms 104 and 105 between the closed and open positions when moved in a linear sliding movement relative to the retractor body 102 as shall be described in greater detail below.

Figure 2:
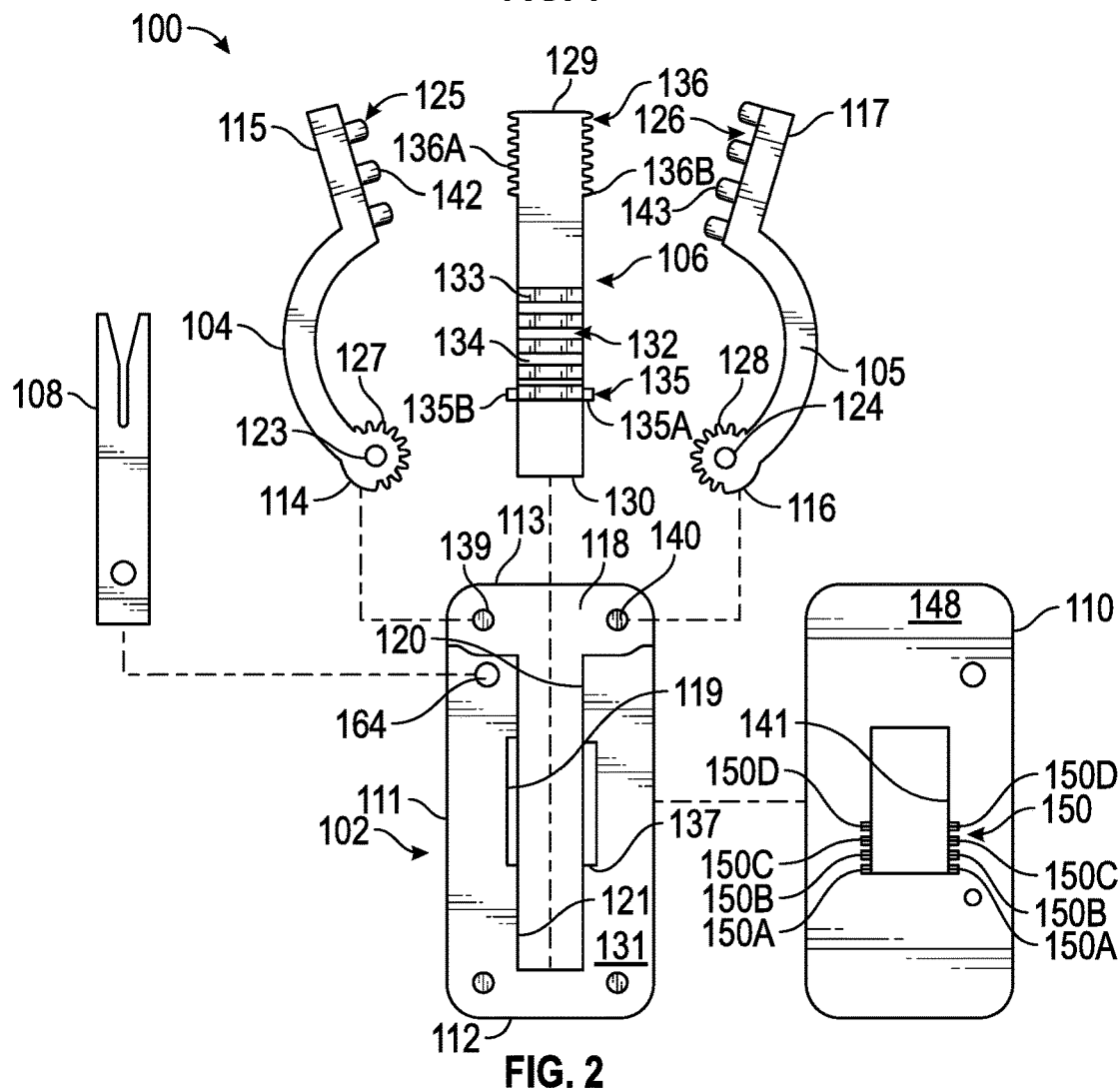
FIG. 2 is an exploded view of the retractor device, according to aspects of the present disclosure.
Figure 3:
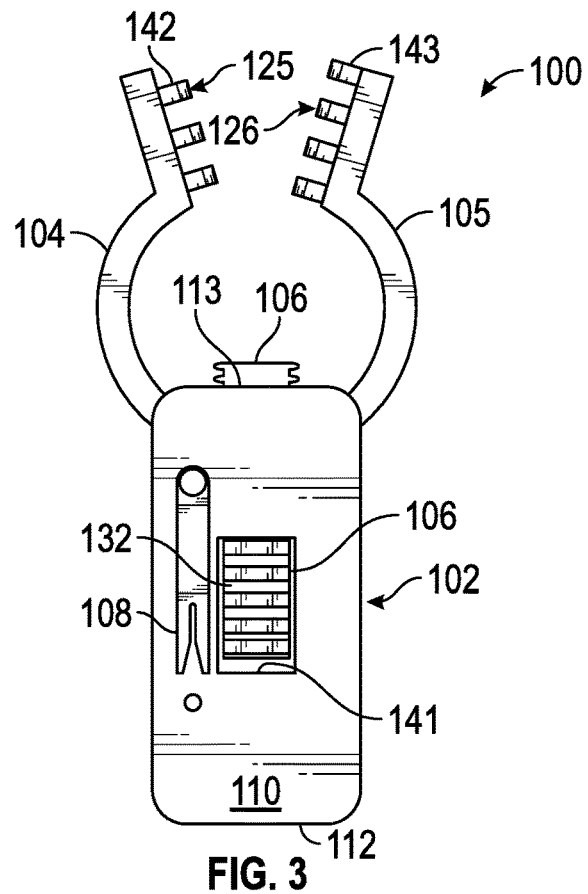
FIG. 3 is a top view of the retractor device, according to aspects of the present disclosure.
Figure 4:
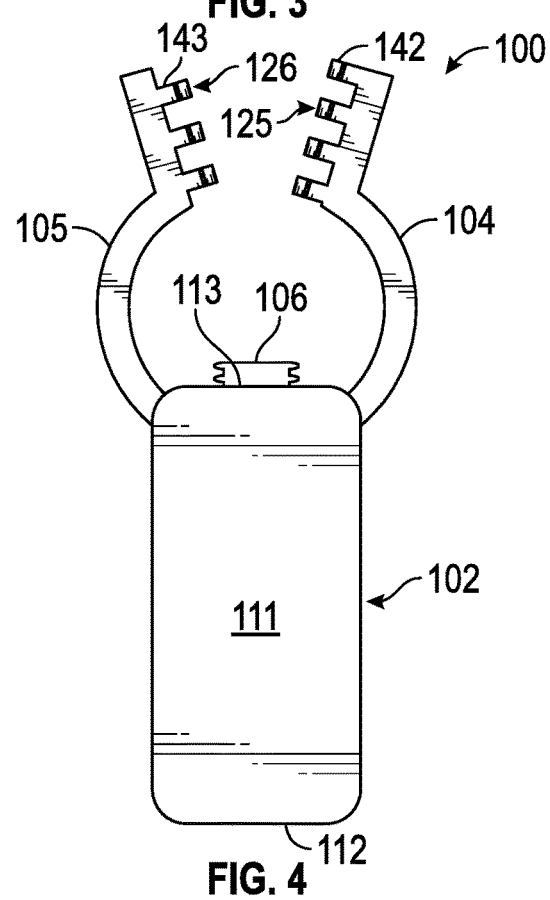
FIG. 4 is a bottom view of the retractor device, according to aspects of the present disclosure.
Figure 5:
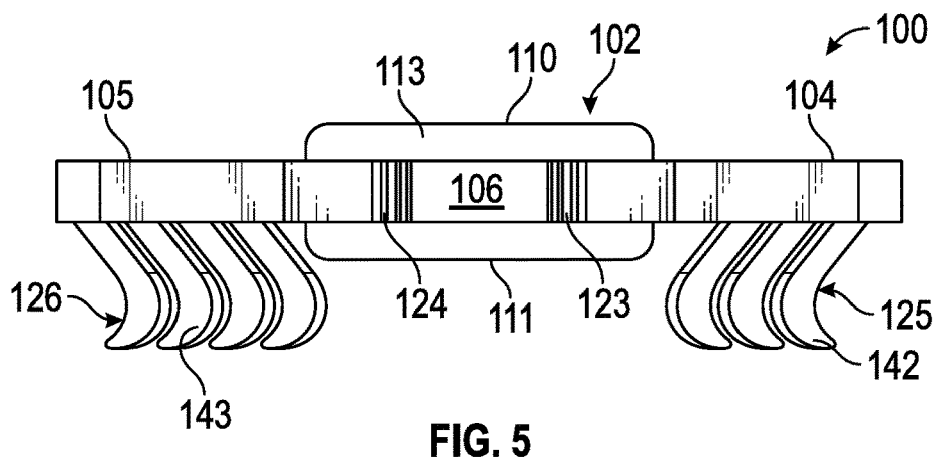
FIG. 5 is an end view of the retractor device, according to aspects of the present disclosure.
Figure 6:
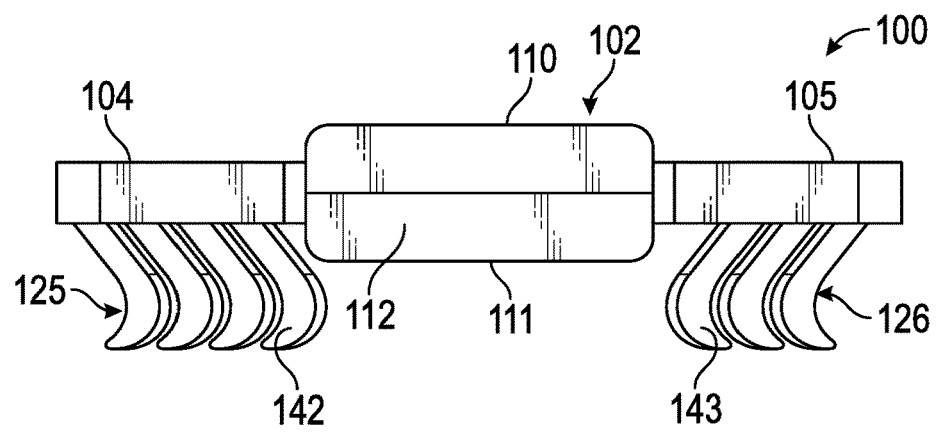
FIG. 6 is an opposite end view of the retractor device, according to aspects of the present disclosure.
Figure 7:
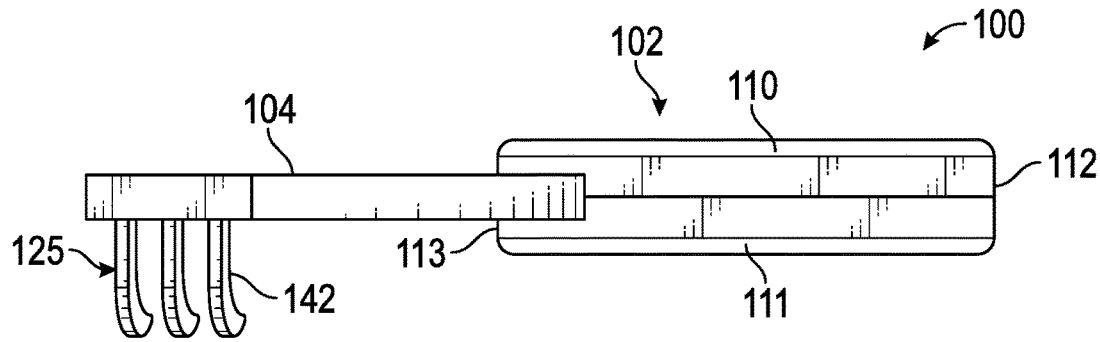
FIG. 7 is a side view of the retractor device, according to aspects of the present disclosure.
Figure 8:
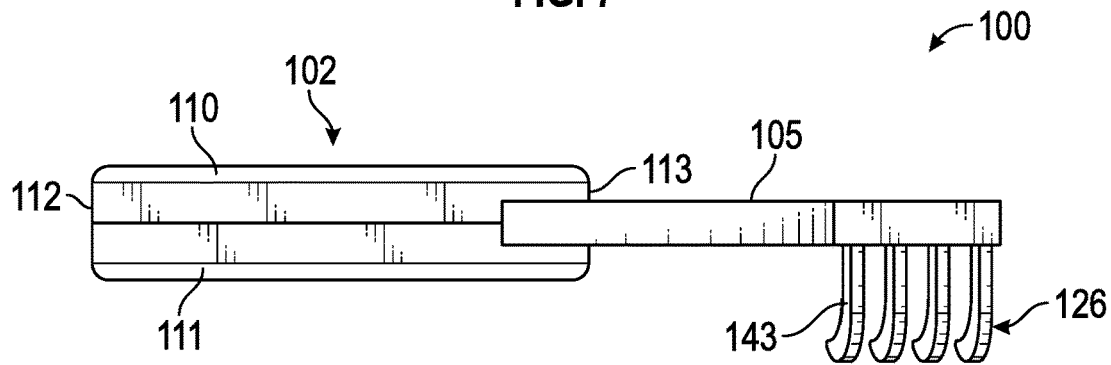
FIG. 8 is an opposite side view of the retractor device, according to aspects of the present disclosure.
Figure 9:
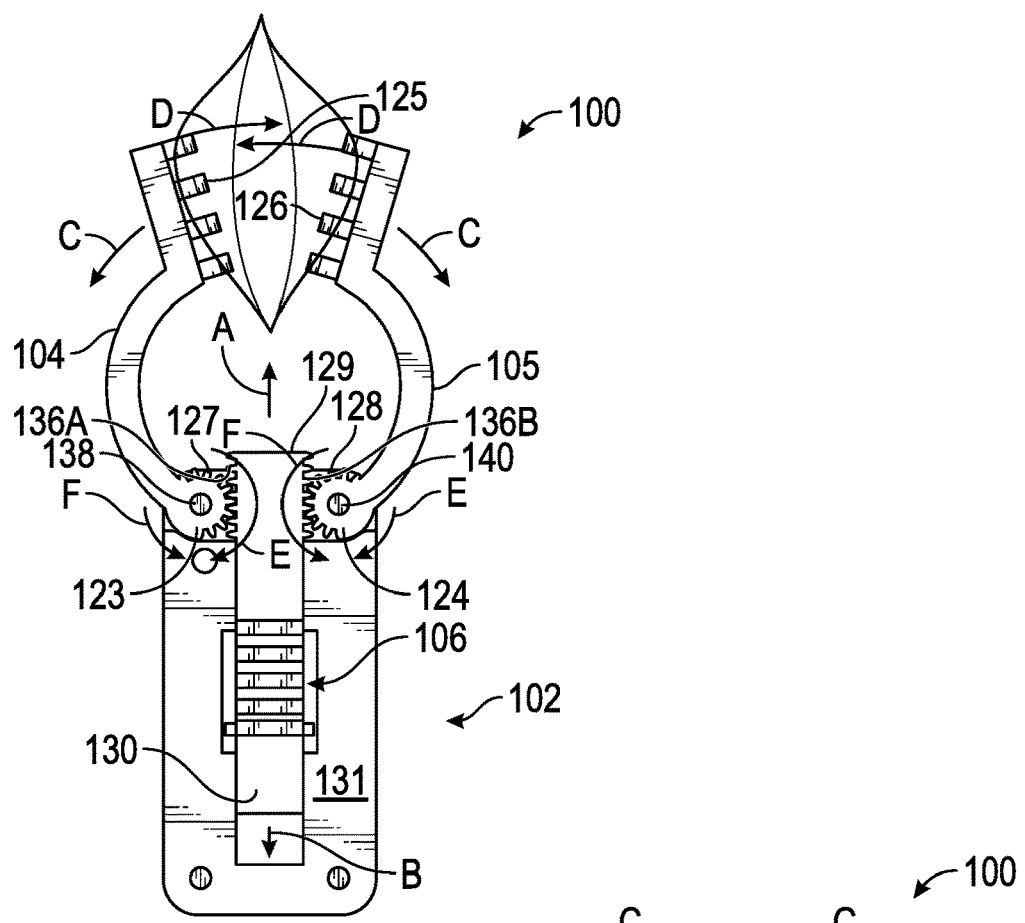
FIG. 9 is a top view showing the interior of the retractor device during operation, according to aspects of the present disclosure.

Referring to FIG. 2, the bottom portion 111 of the retractor body 102 forms an interior surface 131 that defines a cavity 119 which communicates with a lower channel 121 at one end of the cavity 119 and an upper channel 120 at the opposite end of the cavity 119. The cavity 119, upper channel 120 and lower channel 121 are collectively defined between the top portion 110 and the bottom portion 111 of the retractor body 102. Alternatively, the retractor body 102 may define an interior portion (not shown) configured to permit axial movement of the sliding rail 106 relative to the retractor body 102. The cavity 119, upper channel 120 and lower channel 121 are configured to receive the sliding rail 106 therein such that the sliding rail 106 may slide in either a first axial direction A or an opposite second axial direction B during operation of the retractor device 100 as shown in FIG. 9. As further shown in FIG. 2, the upper channel 120 communicates with an open slot 118 formed along the distal end 113 of the retractor body 102 in which respective pinion portions 123 and 124 of the first and second retractor arms 104 and 105 are rotatably attached. The top portion 110 of the retractor body 102 defines an interior surface 148 that forms the cavity 119, upper channel 120 and lower channel 121 of the retractor body 102 when the top portion 110 is attached to the bottom portion 111. The top portion 110 further defines a rectangular-shaped window 141 having a plurality of raised ridges 150 with a first plurality of raised ridges 150A-D aligned in an array along one side of the window 141 and a second corresponding plurality of raised ridges 150A-D aligned in an array positioned along an opposite side of the window 141. The first and second plurality of raised ridges 150A-D defined along the top portion 110 of the retractor body 102 are configured to be engaged to respective lateral ratchet portions 135A and 135B formed at the end of the sliding rail 106 as shall be discussed in greater detail below.

Referring to FIGS. 1 and 2, the first retractor arm 104 defines a proximal end 114 and a distal end 115 in which a gripping surface 125 is formed at the distal end 115 and the pinion portion 123 is formed at the proximal end 114 thereof. Similarly, the second retractor arm 105 also defines a proximal end 116 and a distal end 117 in which a gripping surface 126 is formed at the distal end 117 and the pinion portion 124 is formed at the proximal end 116 thereof. As shown specifically in FIG. 1, in some embodiments the gripping surfaces 125 and 126 may each define a plurality of curved hook members 142 and 143, respectively, configured to grip and retain bodily tissue when retracting an incision. As shown in FIG. 2, the pinion portion 123 of the first retractor arm 104 may be rotatably coupled to pivot rod 139 extending from the bottom portion 111 of the retractor body 102 for swiveling the first retractor arm 104, while the pinion portion 124 of the second retractor arm 105 may be rotatably coupled to a pivot rod 140 for also swiveling the second retractor arm 105 such that the first and second retractor arms 104 and 105 may be swiveled between the closed and open positions and positions there between.

Referring to FIGS. 2 and 9, the pinion portion 123 of the first retracting arm 104 forms a generally round configuration that defines a plurality of radially extending ratchet teeth 127 configured to engage the lateral ratchet teeth 136A formed on one side of the sliding rail 106, while the pinion portion 124 of the second retracting arm 105 also forms a generally round configuration that defines a plurality of radially extending ratchet teeth 128 configured to engage lateral ratchet teeth 136B formed on an opposite side of the sliding rail 106.

Figure 10:
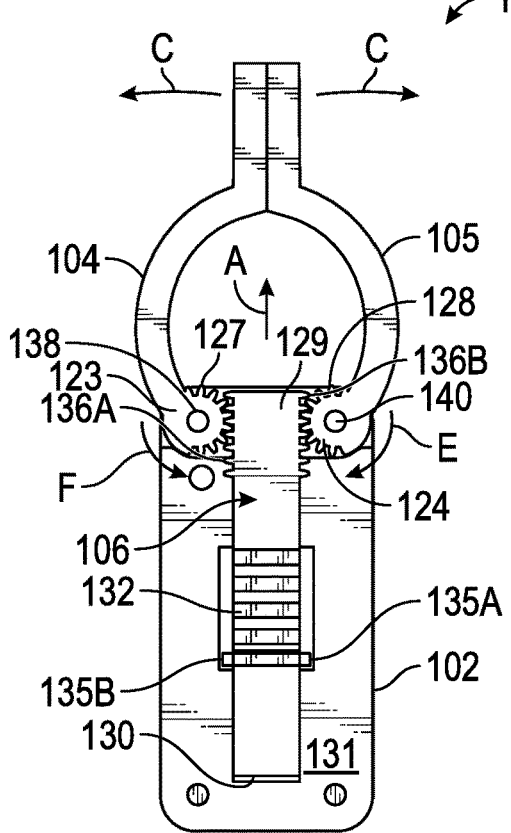
FIG. 10 is a top view showing the retractor arms of the retractor device in a closed position, according to aspects of the present disclosure.
Figure 11:
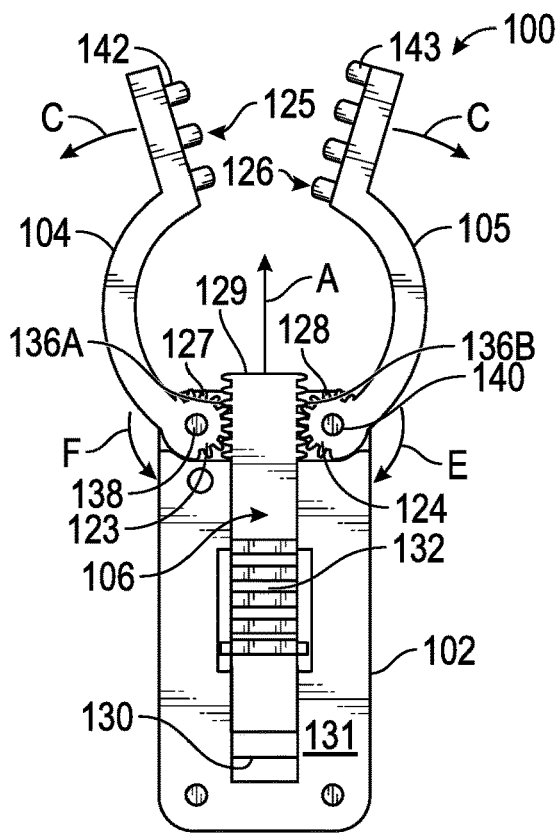
FIG. 11 is a top view showing the retractor arms of the retractor device in an intermediate open position, according to aspects of the present disclosure.
Figure 12:
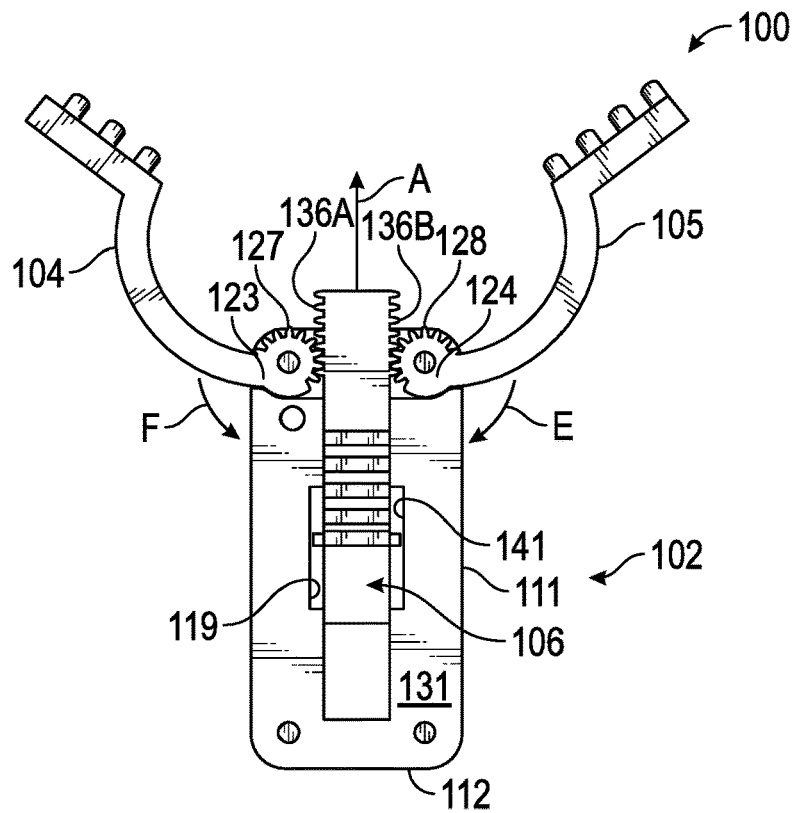
FIG. 12 is a top view showing the retractor arms of the retractor device in an open position, according to aspects of the present disclosure.
Figure 13:
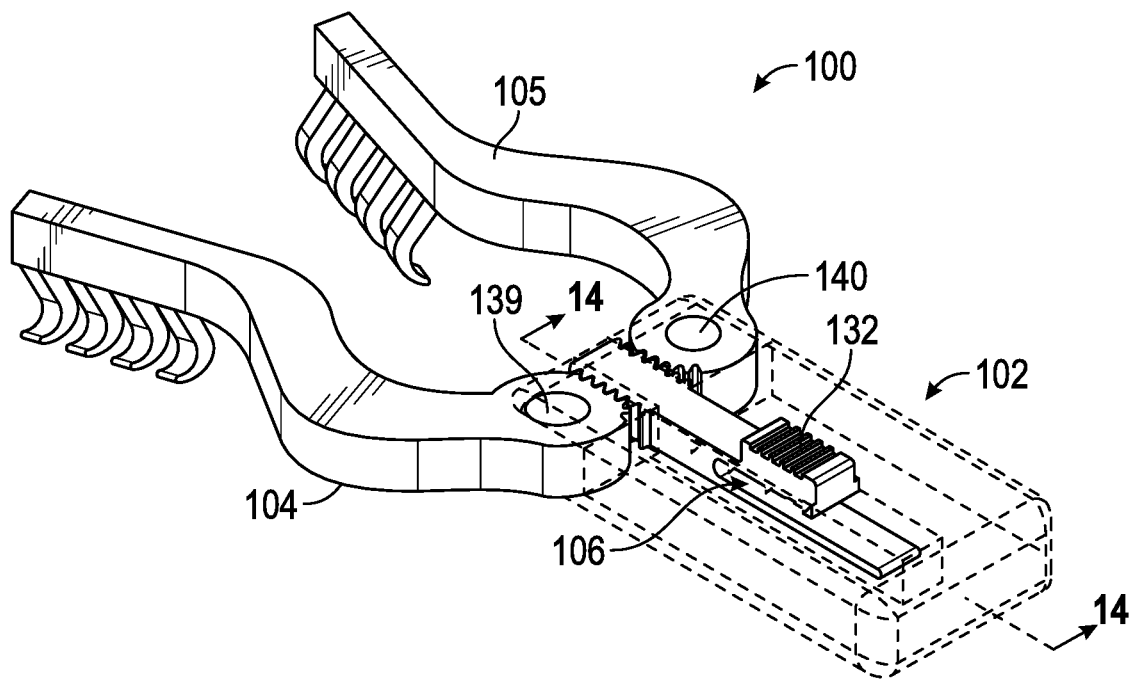
FIG. 13 is a perspective view of the retractor device showing the retractor body in phantom line to illustrate the movement of the sliding rail disposed inside the retractor body, according to aspects of the present disclosure.

As further shown in FIG. 9, axial movement of the sliding rail 106 relative to the retractor body 102 along axial direction A and opposite axial direction B is operable to swivel the first and second retracting arms 104 and 105 to any position between the closed position (FIG. 10) and the open position (FIG. 12). For example, movement of the sliding rail 106 in axial direction A causes the pinion portion 127 of the first retracting arm 104 to rotate in a counterclockwise direction F and the pinion portion 128 of the second retracting arm 105 to concurrently rotate in a clockwise direction E such that the first and second retracting arms 104 and 105 move away from each other along directions C as shown in FIG. 9 until the open position is reached (FIG. 12). Conversely, movement of the sliding rail 106 in axial direction B causes the pinion portion 127 of the first retracting arm 104 to rotate in a clockwise direction E and the pinion portion 128 of the second retracting arm 105 to concurrently rotate in a counterclockwise direction F such that the first and second retracting arms 104 and 105 swivel away other along directions D as shown in FIG. 9 until the closed position is reached (FIG. 10).

Figure 16:
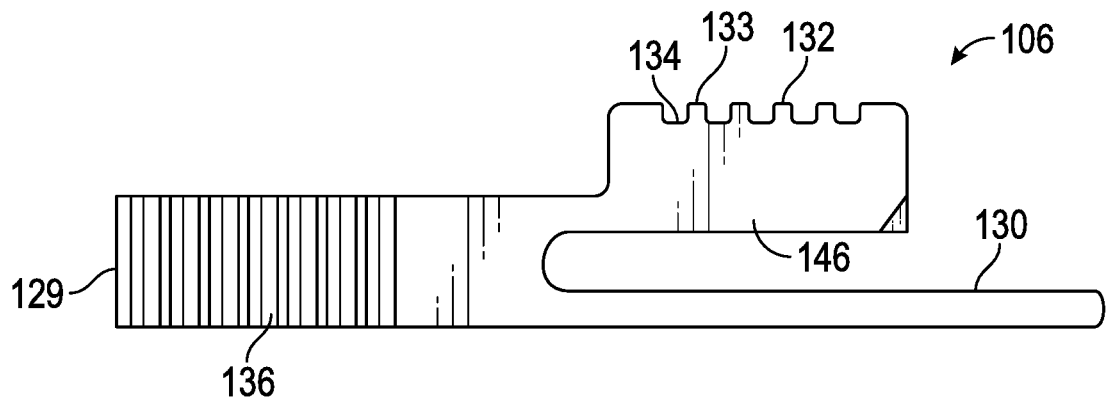
FIG. 16 is a side view of the sliding rail, according to aspects of the present disclosure.
Figure 17:
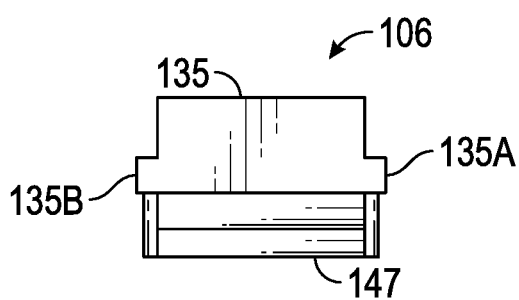
FIG. 17 is a front view of the sliding rail, according to aspects of the present disclosure.
Figure 18:
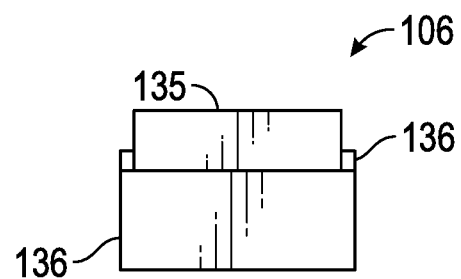
FIG. 18 is a rear view of the sliding rail, according to aspects of the present disclosure.

Referring to FIGS. 15-18, as noted above the sliding rail 106 is operable to engage the pinion portions 127 and 128 to swivel the first and second retractor arms 104 and 105 when the sliding rail 106 is moved in either axial directions A or B. As shown, the sliding rail 106 defines an elongated body having a distal end 129 and a proximal end 130. The distal end 129 of the sliding rail 106 forms opposing lateral ratchet teeth 136, and in particular opposing lateral ratchet teeth 136A and 136B that are formed on opposite sides of the sliding rail 106 along the distal end 129 thereof. As shown in FIG. 9, the lateral teeth 136A of the sliding rail 106 engages the pinion portion 123 while the lateral teeth 136B of the sliding rail 106 simultaneously engages the pinion portion 124 when swiveling the first and second retractor arms 104 and 105. Referring to FIG. 16, the proximal end 130 of the sliding rail 106 defines an upper arm portion 146 that forms a button 132 configured to extend through the window 141 of the retractor body 102 and a lower arm portion 147 that extends in parallel relation with the upper arm portion 146. As further shown, the lower arm portion 147 is separated from the upper arm portion 146 by a space 149 which produces a cantilevered relationship with the upper arm portion 146. As such, the separation of the upper arm portion 146 from the lower arm portion 147 by space 149 allows the upper arm portion 146 to be bent or deflected downward toward the lower arm portion 147 when a downward force is applied to the button 132 by the user. In some embodiments, the button 132 defines a series of alternating raised ridges 133 and grooves 134 that collectively provide a gripping surface for the user to press downward to disengage the lateral ratchet portion 135 of the sliding rail 106 from the respective plurality of ridges 150A-D.

Figure 14A:
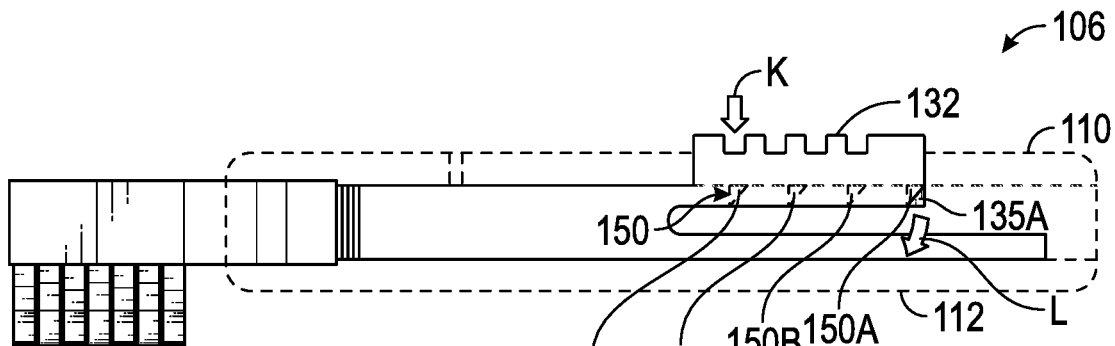
FIG. 14A is a cross-sectional view of the retractor device in a closed configuration taken along line 14-14 of FIG. 13.
Figure 14B:
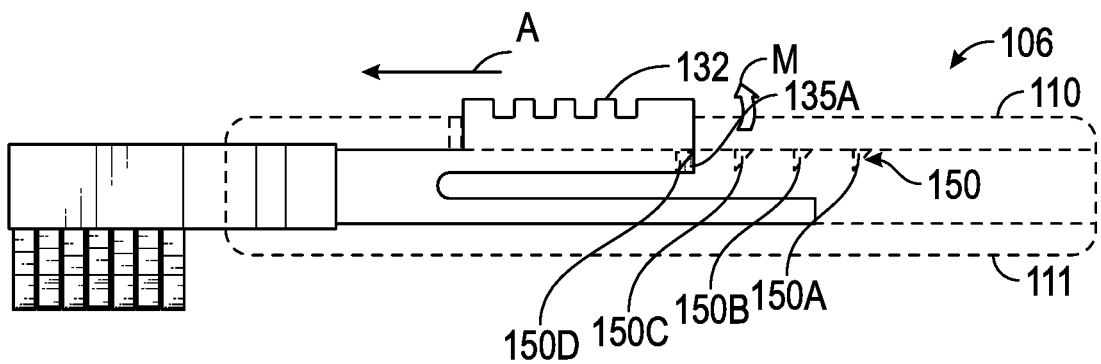
FIG. 14B is across-sectional view of the retractor device in the open position showing the actuation of the button along the sliding rail, according to aspects of the present disclosure.
Figure 15:
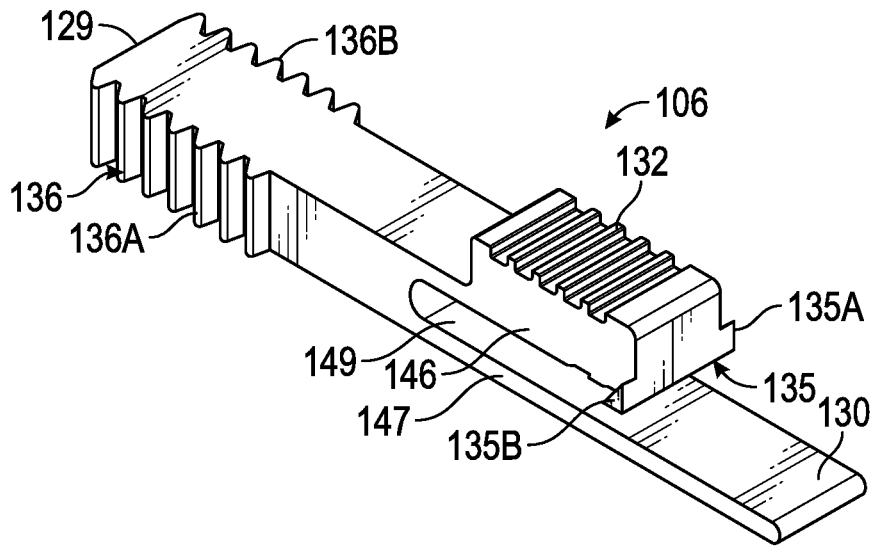
FIG. 15 is a perspective view of the sliding rail, according to aspects of the present disclosure.

As shown in FIGS. 2 and 15-18, the free end of the upper arm portion 146 defines opposite lateral ratchet portions 135A and 135B which are configured to engage one of the first and second corresponding plurality of ridges 150A-D formed on respective opposite sides of the window 122 along the interior surface 148 of the top portion 110 of the retractor body 102. As shown in FIG. 14A, in a closed position the opposite lateral ratchet portions 135 are engaged to the most rearward ridges 150A of the first and second plurality of corresponding ridges 150A-D formed along the top portion 110 of the retractor body 102 such that the sliding rail 106 is fully disposed within the retractor body 102. As shown, a user depressing the button 132 downward along direction K disengages the opposite lateral ratchet portions 135 from the most rearward ridges 150A of the first and second plurality of corresponding ridges 150A-D and causes the upper arm portion 146 to deflect downward in direction L. Referring to FIG. 14B, the user then moves the sliding rail 106 along axial direction A and then reengages the sliding rail 106 as the upper arm portion 146 deflects upwardly along direction M to engage with any one of the other corresponding plurality of ridges 150B, 150C or 150D. For example, moving the sliding rail 106 and engaging the lateral ratchet portions 135 to the most forward ridges 150D swivels the first and second retractor arms 104 and 105 to the open position such that the distal end 129 of the sliding rail 106 extends outwardly from the distal end 113 of the retractor body 102. As such, depressing the button 132 and moving the sliding rail 106 axially in either directions A or B causes the lateral ratchet teeth 136 defined at the distal end 129 of the sliding rail 106 to rotate the ratchet teeth 127 and 128 of respective pinion portions 123 and 124 and cause the first and second retractor arms 104 and 105 to swivel. In some embodiments, the plurality of corresponding ridges 150 may have two corresponding plurality of ridges 150A and 150D that provide only two positions for the sliding rail 106 engage such that the first and second retractor arms 104 and 105 may only swivel between a closed and open positions, or alternatively, other embodiments of the retractor device 100 may include three or more corresponding plurality of ridges 150 for the sliding rail 106 to engage such that the first and second retractor arms 104 and 105 may assume one or more intermediate swivel positions between the open and closed positions.

Figure 22:
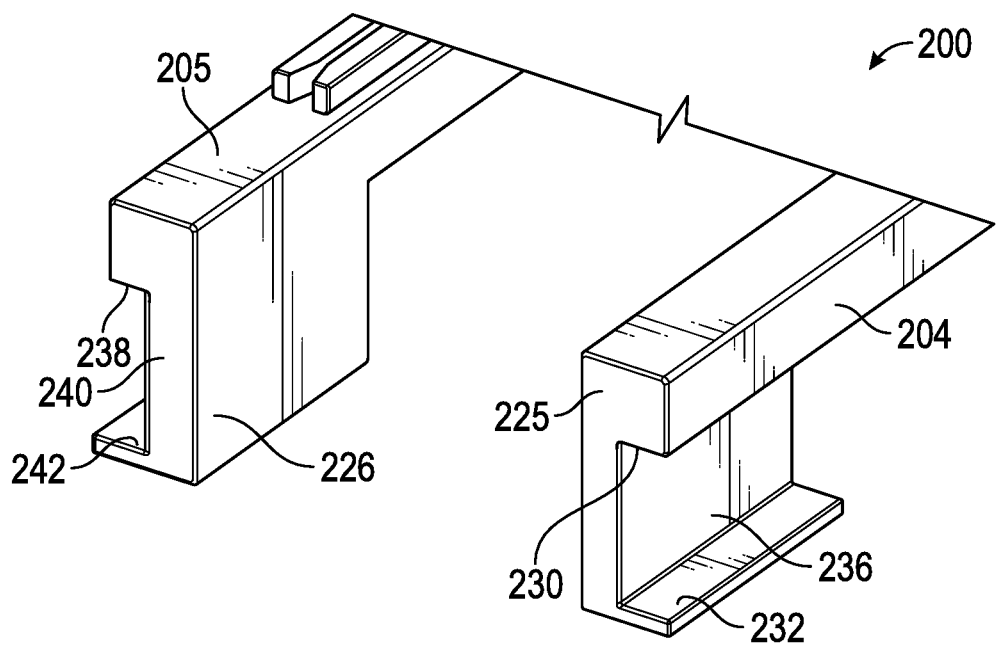
FIG. 22 is an enlarged view of a second embodiment of the first and second retracting arms of the retractor device, according to aspects of the present disclosure.

Referring to FIG. 22, an alternative embodiment of the retractor device, designated 200, is illustrated. In this embodiment, the retractor device 200 has substantially the same structure and operation as the retractor device 100 except that the first and second retracting arms 204 and 205 define differently configured first and second gripping surfaces 225 and 240. As shown, the first gripping surface 225 of the first retractor arm 204 defines a middle portion 236 formed between upper and lower shoulders 230 and 232 that collectively define a surface to engage and retract an incision along the skin, muscle or other bodily tissues. Similarly, the second gripping surface 240 defines a middle portion 226 formed between upper and lower shoulders 238 and 242 that also collectively define a surface to engage and retract an incision along the skin, muscle or other bodily tissues.

As described above, certain surgical procedures (such as ventriculoperitoneal shunt insertions and revision procedures) require the use of non-rigid and implantable catheters that divert fluid from one body space to either the external environment or to another body space. It is desirable to maintain a shunt in place during a procedure in order to resist movement of the shunt in and out of an incision. Referring back to FIG. 1, as noted above the retractor device 100 may include a shunt retainer 108 movably engaged to the retractor body 102 and configured to be engaged and retain tubing, such as a shunt tubing or catheter, in a fixed stationary position relative to the retractor device 100. In some embodiments, the shunt retainer 108 is rotatably coupled to the retractor body 102 by a securing member 164 inserted through the shunt retainer 108 and retractor body 102. In some embodiments securing member 164, may be a non-metal nylon pin, screw, or the like. The shunt retainer 108 may be oriented by rotating the shunt retainer 108 to the desired orientation. It should be understood that the shunt retainer 108 may be similarly positioned along different locations of the retractor body 102 or other portions of the retractor device 100 as desired. As shown, the shunt retainer 108 may include the opening 160 for receiving the securing member 164 (FIG. 1) to engage the shunt retainer 108 along the retractor body 102 and permit the shunt retainer 108 to swivel along directions J as shown. The shunt retainer 108 may be made from the same or similar non-metallic materials as the retractor device 100, described herein. As such, the shunt retainer 108 does not interfere with EM systems and may be implemented to maintain portions of a shunt in a stationary position relative to the retractor body 102 and the patient.

Figure 19:
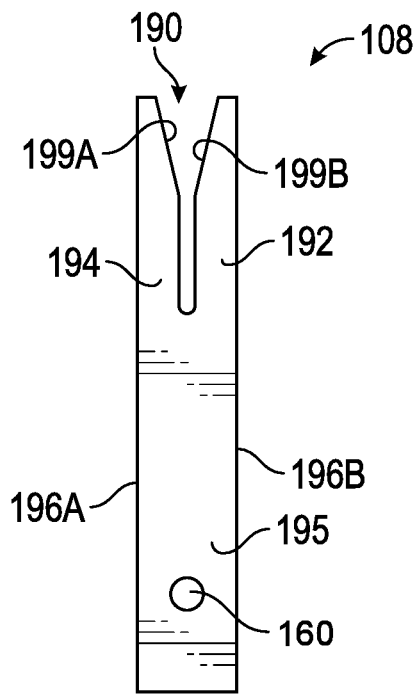
FIG. 19 is a top view of the embodiment of the shunt retainer shown in FIG. 1, according to aspects of the present disclosure.

As further shown in FIG. 19, one embodiment of the shunt retainer 108 includes a base 195 defining a first lateral side 196A and a second lateral side 196B formed opposite the first lateral side of 196A. The shunt retainer 108 further defines a first member 194 extending from the first lateral side 196A of the base 195 and a second member 192 extending from the second lateral side 196B of the base 195. In some embodiments, the second member 192 is oriented in parallel relation relative to the first member 194 as shown. A Y-shaped channel 190 may be defined between the first member 194 and the second member 192 of the shunt retainer 108. In some embodiments, the Y-shaped channel 190 defines a proximal section 199A and a distal section 199B that is wider than the proximal section 199A which are configured to engage and retain tubing within the Y-shaped channel 190. In the embodiment shown, the circular shape of the opening 160 formed along the shunt retainer 108 substantially corresponds to the circumference and shape of the securing member 164. Accordingly, the shunt retainer 108 is configured to pivot or rotate laterally or move around or about a fixed point defined by the securing member 164 by virtue of the dimensions of the opening 160 as shown in FIG. 1.

Figure 20:
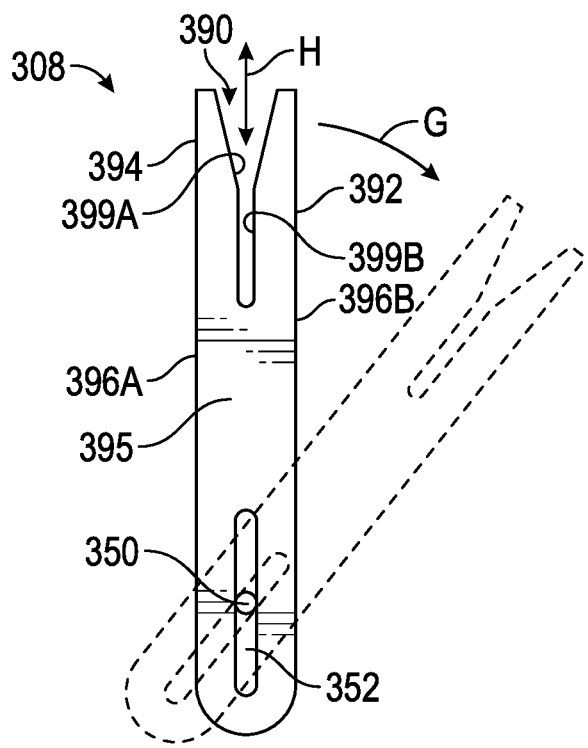
FIG. 20 is a top view of a second embodiment of a shunt retainer, according to aspects of the present disclosure.
Figure 21:
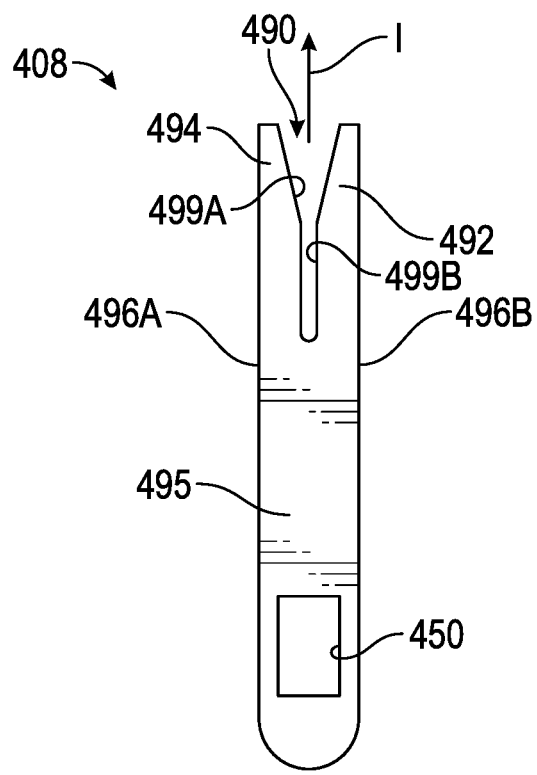
FIG. 21 is a top view of a third embodiment of a shunt retainer, according to aspects of the present disclosure.

Referring to FIGS. 20 and 21, alternative embodiments of a shunt retainer are contemplated. For example, FIG. 20 shows an embodiment of the shunt retainer 308 having a base 395 defining a first lateral side 396A and a second lateral side 396B formed opposite the first lateral side 396A. The shunt retainer 308 further defines a first member 394 extending from the first lateral side 396A of the base 395 and a second member 392 extending from the second lateral side 396B of base 395. In some embodiments, the second member 392 is oriented in parallel relation relative to the first member 394 as shown. A Y-shaped channel 390 may be defined between the first member 394 and the second member 392 of the shunt retainer 308. In some embodiments, the Y-shaped channel 390 defines a proximal section 399A and a distal section 399B that is wider than the proximal section 399A which are configured to engage and retain tubing within the Y-shaped channel 390. In this embodiment, however, the shunt retainer 308 may define a slot 352 as opposed to the opening 160 of the shunt retainer 108. The slot 352 may accommodate different degrees of movement of the shunt retainer 308 about a retractor device 100, such as axial movement H or swivel movement G, as indicated.

As shown in FIG. 21, another embodiment of a shunt retainer 408 includes a base 495 defining a first lateral side 496A and a second lateral side 496B formed opposite the first lateral side 496A. The shunt retainer 408 further defines a first member 494 extending from the first lateral side 496A of the base 495 and a second member 492 extending from the second lateral side 496B of base 495. In some embodiments, the second member 492 is oriented in parallel relation relative to the first member 494 as shown. A Y-shaped channel 490 may be defined between the first member 494 and the second member 492 of the shunt retainer 408. In some embodiments, the Y-shaped channel 490 defines a proximal section 499A and a distal section 499B that is wider than the proximal section 399A which are configured to engage and retain tubing within the Y-shaped channel 490. In this embodiment, however, the shunt retainer 308 may define a rectangular opening 450 which may also accommodate different degrees of movement of the shunt retainer 408, such as axial movement I, as indicated.

The retractor device 100 of the present inventive concept may be manufactured entirely from a non-metal material, or combinations thereof such as a plastic, rubber, nylon, glass fiber, a polymer-based biocompatible material, a bioactive material, a resin, ceramic composites, or any material that does not cause interference with EM-guidance systems. In some embodiments, materials used to form the retractor device 100 may include polymers such as Ixef® polyacrylamide (PARA), AvaSpire® polyaryletherketone (PAEK), and may include Acrylonitrile butadiene styrene (ABS). Because the retractor device 100 is made from such nonmetal materials, the retractor device reduces or avoids interference with EM systems. The retractor device 100 is further biocompatible and reduces the chance of inflicting harm around an incision or causing inflammation. In addition, the retractor device 100 is much lighter in weight as compared with conventional metallic retractors, is cheaper to manufacture, is disposable, and meets predefined mechanical engineering requirements and preferred surgical specifications, as further described herein. In one embodiment, a PARA 50% glass fiber composite may be utilized for the retractor device 100, which accommodates surgical biomedical environments, and is structurally sufficient for the desired retraction operations described herein.

The surfaces of the retractor device 100 and various components are depicted as substantially smooth. However, it is contemplated that the nonmetal retractor device 100 may have surface features such as ridges, bumps, protrusions, channels or any combination of these elements without departing from the scope of the disclosure. These features may be advantageous for interacting with the subject's skin and muscle tissue and substantially increasing gripping capacity. In addition, these features may be dispersed across the device in any known configuration to the preference of the user.

The retractor device 100 may be manufactured using 3D printing methods by printing and connecting various discrete components, injection molding, or by unitary construction or combinations thereof. Indeed, the device's structure suits 3D printing methods because it is relatively inexpensive to print, and retains the structural integrity of non-3D printed devices. It is also contemplated that the non-metallic retractor device 100 may have a mirrored configuration to what is depicted in the figures, which would allow the retractor device 100 to be used from the right or the left side of the incision. Alternatively, the arm 110 and the second segment 108 may extend along different angles, either independently or parallel to each other. In some embodiments, the retractor device 100 may be manufactured such that any interior part of the device is hollow. For example, the retractor body 102 may be constructed hollow so that is a lighter weight and uses less manufacturing material.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:
1. A medical device, comprising:
a retractor body defining an interior portion, the retractor body forming a window and defining a plurality of ridges formed proximate the window along an interior surface of the retractor body;
a sliding rail in operative engagement with the retractor body and disposed within the interior portion of the retractor body, wherein the sliding rail is operable to move within the interior portion of the retractor body in a first direction or a second direction opposite the first direction;
a first retracting arm having a distal end that forms a first gripping surface and a proximal end in operative engagement with the sliding rail, wherein the proximal end of the first retractor arm is rotatably mounted to the retractor body; and
a second retracting arm having a distal end that forms a second gripping surface and a proximal end in operative engagement with the sliding rail, and wherein the proximal end of the second retractor arm is rotatably mounted to the retractor body;
wherein actuation of the sliding rail in the first direction within the interior portion of the retractor body causes the first and second retracting arms to swivel relative to the retractor body, and wherein the retractor body, sliding rail and first and second retractor arms comprise a non-metallic material.

2. The medical device of claim 1, wherein the non-metallic material comprises a glass fiber material.

3. The medical device of claim 1, further comprising:
a shunt retainer mechanically coupled to the retractor body, the shunt retainer configured to engage tubing.

4. The medical device of claim 3, wherein the shunt retainer is movably coupled to the retractor body.

5. The medical device of claim 3, wherein the shunt retainer comprises:
a base defining a first lateral side and a second lateral side formed opposite the first lateral side;
a first portion extending from the first lateral side of the base; and
a second portion extending from the second lateral side of the base, the second member oriented in parallel relation relative to the first member.

6. The medical device of claim 5, wherein the shunt retainer further comprises:
a Y-shaped channel defined between the first portion and the second portion of the shunt retainer, the Y-shaped channel defining a proximal section and a distal section wider than the proximal section; and
wherein the shunt retainer is configured to receive a tubing through the distal section of the Y-shaped channel and occlude the shunt tubing along the proximal section of the Y-shaped channel.

7. The medical device of claim 1, wherein the sliding rail further comprises a distal end that forms opposing lateral ratchet teeth and a proximal end that forms a lateral ratchet portion.

8. The medical device of claim 7, wherein the proximal end of the sliding rail comprises an upper arm portion that defines a button and a lower arm portion that extends in parallel relation relative to the upper arm portion.

9. The medical device of claim 7, further comprising:
a first pinion defined along the proximal end of the first retracting arm; and
a second pinion defined along the proximal end of the second retracting arm,
wherein the first pinion is configured to engage one portion of the lateral ratchet teeth of the sliding rail and the second pinion is configured to engage another portion of the lateral ratchet teeth of the sliding rail such that movement of the sliding rail in a first direction rotates the first pinion in a first rotational direction and the second pinion in a second rotational direction opposite that of the first rotational direction, wherein movement of the sliding rail in a second direction opposite that of the first direction rotates the first pinion in the second rotational direction and the second pinion in the first rotational direction.

10. The medical device of claim 8, wherein the lateral ratchet portion of the sliding rail is configured to be engaged with one of the plurality of ridges to fix the sliding rail in a stationary position relative to the retractor body, and wherein actuation of the button deflects the sliding rail to disengage the lateral ratchet portion from the lateral ratchet portion and permit movement of the sliding rail relative to the retractor body.

11. The medical device of claim 10, wherein engagement of the sliding rail from one of a plurality of ridges to another one of the plurality of ridges causes the first and second retractor arms to swivel relative to the retractor body.

12. The medical device of claim 1, wherein movement of the sliding rail in a first direction causes the first and second retracting arms to swivel in a first direction and wherein movement of the sliding rail in a second direction opposite the direction of the first direction causes the first and second retracting arms to swivel in an opposite second direction.

13. The medical device of claim 1, wherein the interior portion of the retractor body is formed by a cavity defined between an upper channel and a lower channel.

14. The medical device of claim 1, wherein the retractor body, the sliding rail, the first retracting arm, and the second retracting arm comprise a material that avoids interference with EM-guidance systems.

15. The medical device of claim 1, wherein the distal end of the first retracting arm defines a first gripping surface and the distal end of the second retracting arm defines a second gripping surface.

16. The medical device of claim 15, wherein the first and second gripping surfaces each define a plurality of hook members or a middle portion formed between an upper shoulder and a lower shoulder.

17. A retractor device comprising:
a retractor body defining an interior portion, the retractor body defining a plurality of ridges formed along an interior surface of the retractor body;
a sliding rail in operative engagement with the retractor body and disposed within the interior portion of the retractor body, wherein the sliding rail is operable to move within the interior portion of the retractor body in a first direction or a second direction opposite the first direction;
a first retracting arm having a distal end that forms a first gripping surface and a proximal end in operative engagement with the sliding rail, wherein the proximal end of the first retractor arm is rotatably mounted to the retractor body; and
a second retracting arm having a distal end that forms a second gripping surface and a proximal end in operative engagement with the sliding rail, and wherein the proximal end of the second retractor arm is rotatably mounted to the retractor body;
wherein actuation of the sliding rail in the direction within the interior portion of the retractor body causes the first and second retracting arms to swivel relative to the retractor body.

18. A method, comprising:
forming a retractor body, the retractor body defining an interior portion and a plurality of ridges defined along the interior portion;
forming a sliding rail having a distal end defining opposing lateral ratchet teeth and a proximal end that forms a lateral ratchet portion
disposing the sliding rail within the interior portion of the retractor body such that the lateral ratchet portion is in operative engagement with one of the plurality of ridges of the retractor body;
forming a first retractor arm having a distal end defining a first gripping surface and a proximal end defining a first pinion portion in operative engagement with the lateral ratchet teeth of the sliding rail;
forming a second retractor arm having a distal end defining a second gripping surface and a proximal end defining a second pinion portion in operative engagement with the lateral ratchet teeth of the sliding rail; and
engaging the lateral ratchet portion of the sliding rail to one of the plurality of ridges defined along the interior portion of the retractor body.

19. The method of claim 18, further comprising:

engaging a shunt retainer along the retractor body;

rotating the shunt retainer relative to the retractor body such that a portion of the shunt retainer extends outside a footprint of the retractor body, the shunt retainer configured to receive a tubing when orientated in the first position; and rotating the shunt retainer to a second position relative to the retractor body such that the shunt retainer is entirely disposed over the footprint of the retractor body to store the shunt retainer.

20. The method of claim 19, further comprising:

engaging a shunt retainer along the retractor body;

rotating the shunt retainer relative to the retractor body such that a portion of the shunt retainer extends outside a footprint of the retractor body, the shunt retainer configured to receive a tubing when orientated in the first position; and rotating the shunt retainer to a second position relative to the retractor body such that the shunt retainer is entirely disposed over the footprint of the retractor body to store the shunt retainer.

\* \* \* \* \*